United States Patent

Brass et al.

[11] Patent Number: 5,840,499
[45] Date of Patent: Nov. 24, 1998

[54] METHOD AND KIT FOR DETECTION OF THROMBIN RECEPTOR ACTIVATION OF PLATELETS AND OTHER CELLS

[75] Inventors: Lawrence Brass, Bala Cynwyd; James A. Hoxie, Berwyn, both of Pa.

[73] Assignee: Trustees of the University of Pennsylvania, Philadelphia, Pa.

[21] Appl. No.: 659,486

[22] Filed: Jun. 6, 1996

Related U.S. Application Data

[63] Continuation-in-part of Ser. No. 220,375, Mar. 31, 1994, abandoned.

[51] Int. Cl.[6] .................... G01N 33/53; G01N 33/543; C07K 7/00; C07K 16/28
[52] U.S. Cl. ................ 435/7.1; 435/7.92; 435/13; 530/300; 530/327; 530/387.1; 436/518
[58] Field of Search ............... 435/7.24, 7.94, 435/13, 975, 7.92, 7.1; 530/300, 327, 387.1; 436/518, 531

[56] References Cited

U.S. PATENT DOCUMENTS 5,256,766   10/1993   Coughlin .......................... 530/327

FOREIGN PATENT DOCUMENTS

WO 92/14750   2/1992   WIPO .

OTHER PUBLICATIONS

Brass, L.F., et al. "Studies Using Monoclonal Antibodies Directed Against A Defined Domain Within The Receptor N Terminus", *J. Biol. Chem.* (1992) 267:13795–13798.
Scarborough R.M., et al. "Tethered Ligand Agonist Peptides", *J. Biol. Chem.* (1992) 267:13146–13149.
Vassallo, R.R. Jr., et al. "Structure–Function Relationships in the Activation of Platelet Thrombin Receptors by Receptor–derived Peptides", *J. Biol. Chem.* (1992) 267:6081–6085.
Vu, T. et al., "Molecular Cloning of a Functional Thrombin Receptor Reveals a Novel Proteolytic Mechanism of Receptor Activation", *Cell* (1991) 64:1057–1068.
Vu, T. et al., "Domains Specifying Thrombin–receptor Interaction", *Nature* (1991) 353:674–677.
Gosling et al. (1990) Clin. Chem. 36:1408–1427.
Norton et al. (1993) Blood 82:2125–2136.

*Primary Examiner*—Stephen Walsh
*Assistant Examiner*—Michael Pak
*Attorney, Agent, or Firm*—Law Offices of Jane Massey Licata

[57] ABSTRACT

Method for detecting thrombin-induced cell activation via a system of detection capable of determining the presence of the cleaved peptide fragment of the thrombin receptor are provided. These methods are used in diagnosing and treating a pre-thrombotic state or thrombotic disorder in a patient. Detection kits to be used with this method are also provided.

3 Claims, 2 Drawing Sheets

METHOD AND KIT FOR DETECTION OF THROMBIN RECEPTOR ACTIVATION OF PLATELETS AND OTHER CELLS

This application is a continuation-in-part of application Ser. No. 08/220,375, filed Mar. 31, 1994, now abandoned.

BACKGROUND OF THE INVENTION

Thrombin is an important activator of both fibrin clot formation and platelet plug formation and plays a central role in hemostasis, thrombosis, and atherosclerosis. Thrombin is an active form of an enzyme normally present in plasma as an inactive precursor, prothrombin. When vascular damage exposes tissue factor to the circulation, prothrombin is converted to thrombin, thus making the enzyme available to activate platelets.

Anticoagulant therapy, such as administration of drugs including heparin and coumadin, has been traditionally directed toward reducing the effects of thrombin either by decreasing levels of circulating prothrombin or by inhibiting the enzymatic activity of thrombin. While these approaches are effective in slowing clot formation, they are not very effective in inhibiting platelet activation.

Platelet plug formation plays a much more dominant role than fibrin clot formation in arterial thrombosis, particularly in coronary arteries. Thrombin-induced platelet formation is especially important for arterial thrombus formation. Imbalances in this process can lead to myocardial infarction and some forms of unstable angina and strokes.

Thrombin is able to evoke responses from a number of the cells located in and around the vascular space, including platelets. These response occur at nanomolar concentrations of thrombin and are mediated by a recently-cloned member of the G protein coupled family of receptors. Like other receptors that interact with G proteins, the thrombin receptor is comprised of a single polypeptide chain with 7 hydrophobic domains, an extended extracellular N-terminus and sites for post-translational processing including palmitoylation of the C-terminus and N-linked glycosylation of the N-terminus. A potential site for cleavage by thrombin was found between residues $Arg^{41}$ and $Ser^{42}$. Vu, T. et al., *Cell* (1991) 64:1057–1068; Vu, T. et al. *Nature* (1991) 353:674–677. Although these receptors resemble others that couple to G proteins, thrombin receptors are activated by a novel mechanism in which the protease cleaves the receptor N-terminus between residues $Arg^{41}$ and $Ser^{42}$, exposing a new N-terminus, referred to as the neo-N-terminus, that serves as a tethered ligand that is capable of activating the receptor. Vu, T. et al., *Cell* (1991) 64:1057–1068. A 14 residue peptide corresponding to residues $Ser^{42}$ through $Phe^{55}$ (SFLLRNPNDKYEPF) was shown to cause platelet aggregation and mutations in the tethered ligand domain and was found to inhibit activation of the expressed receptor. Vu, T. et al., *Cell* (1991) 64:1057–1068; Scarborough R. M., et al. *J. Biol. Chem.* (1992) 267:13146–13149. Receptor-derived peptides can evoke many, if not all, of the effects of thrombin on platelets, as well as a variety of other cells that are located in and around the vascular space, including fibroblasts, vascular smooth muscle cells and endothelial cells. The first 6 residues of the tethered ligand domain, SFLLRN, have been found to be sufficient to activate the receptor and antibodies directed against this domain have been found to inhibit platelet activation by thrombin. Vassallo, R. R. Jr., et al. *J. Biol. Chem.* (1992) 267:6081–6085; Brass, L. F., et al. *J. Biol. Chem.* (1992) 267:13795–13798.

The identification and characterization of the thrombin receptor has permitted the rational design of agents expected to regulate thrombin activity and systems to evaluate these agents to determine their effects on thrombosis in the cardiovascular system. In addition, diagnostic assays have been developed for assessing cardiovascular status.

In PCT/US92/01312 (Coughlin et al.) methods and materials useful in the regulation of the cardiovascular system in mammals are provided. Transfected cells which can be cultured so as to display the thrombin receptor on their surface (thus providing an assay system for the interaction of materials with native thrombin receptor) are disclosed. In one embodiment of their invention, Coughlin et al. suggest that the availability of the recombinant thrombin receptor protein permits production of antibodies which are immunospecific to the activated form of the receptor. These antibodies can be used for diagnostic imaging of activated receptor in vivo or to detect and measure the presence of activated receptor in body fluids.

In contrast to the prior art, which has focused on methods of detection based upon the presence or absence of activated thrombin receptor, a method has now been developed for detection of thrombin-induced cell activation by detecting the cleaved peptide fragment of the thrombin receptor. These methods of the present invention can be used to diagnose pre-thrombotic states in patients.

SUMMARY OF THE INVENTION

An object of the invention is to provide a method of detecting thrombin-induced cell activation which comprises contacting a sample with a system of detection which is capable of measuring the presence of a cleaved peptide fragment of a thrombin receptor and detecting the presence or absence of the cleaved peptide fragment.

Another object of the invention is to provide a method of diagnosing a pre-thrombotic state in a patient comprising a sample, preferably a biological fluid, from a patient, contacting the sample with a system of detection capable of measuring the presence of a cleaved peptide fragment of a thrombin receptor, detecting the presence or absence of the cleaved peptide fragment of a thrombin receptor, and quantifying the cleaved peptide fragment of the thrombin receptor so that a pre-thrombotic state in the patient can be diagnosed.

DETAILED DESCRIPTION OF THE INVENTION

Figure 1:
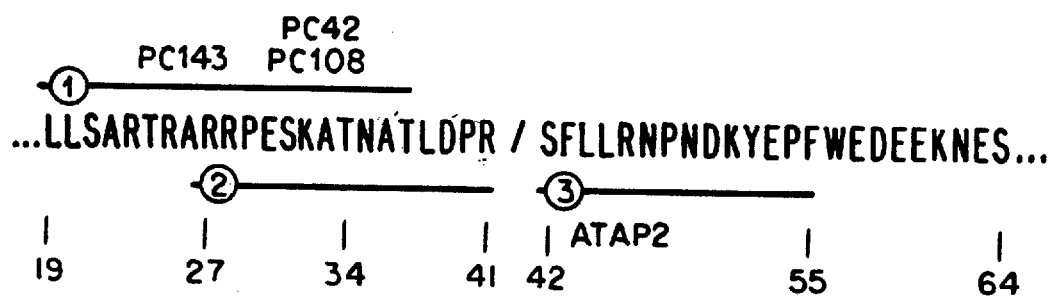
FIG. 1 provides the sequence of residues 19 through 64 of the human thrombin receptor (SEQ ID NO: 1) and indicates the portions of the receptor referred to as Peptide 1 (SEQ ID NO: 2) and Peptide 2 (SEQ ID NO: 3) in the specification and the cleavage site between residues 41 and 42. Antibody labels PC42, PC143 and PC108 mark the approximate location of the antibody epitopes based upon ELISA results with these peptides.

As an activator of both fibrin clot formation and platelet plug formation, thrombin plays a central role in hemostasis, thrombosis and atherosclerosis. Although these events have been studied for many years, it is only within the past few years that the mechanism by which thrombin activates platelets and other vascular cells has been determined.

Thrombin is present in the plasma as the inactive precursor, prothrombin. Upon activation, thrombin is able to evoke responses from a number of the cells located in and around the vascular space, including platelets. At nanomolar concentrations, thrombin is able to cause platelet activation, aggregation and secretion. These processes are only modestly inhibited by aspirin. Thrombin activates thrombin receptors by a novel mechanism wherein the thrombin cleaves its receptor N-terminus between residues $Arg^{41}$ and $Ser^{42}$, exposing a new N-terminus, referred to as the "neo-N-terminus". The neo-N-terminus serves as a tethered ligand that is capable of activating the receptor.

When thrombin cleaves the exposed N-terminus of its receptor between residues $Ser^{42}$ and $Arg^{41}$, a peptide fragment containing the original N-terminus is created. Little is known about this fragment as most work in this area has focused on the activated thrombin receptor. This cleaved peptide fragment may be as long as 30 amino acids in length after taking into account the presence of a signal peptide and may have a mass up to several kDA. Until now it was not known whether the peptide fragment was lost from the cell surface or retained by the cell in another form or location. It has now been found that the presence of the cleaved peptide fragment is detectable in biological fluids and can be used as a marker for thrombin receptor activation on platelets and other vascular cells. Methods of detecting this cleaved peptide are provided in the present invention. Such methods are useful in the diagnosis and treatment of patients with pre-thrombotic and thrombotic disorders, including disseminated intravascular coagulation. Detection of states contributing to atherosclerotic cardiovascular disease can also be achieved with the methods of the present invention. In addition, these methods may used to screen agents and assess their ability to affect thrombin-induced cell activation.

In the present invention a method is provided for detection of thrombin-induced cell activation in a sample which comprises contacting the sample with a system of detection which is capable of measuring the presence of a cleaved peptide fragment of a thrombin receptor and detecting the presence or absence of the cleaved peptide fragment. Such methods can be used to diagnose a pre-thrombotic state in a patient. A sample comprising a biological fluid, preferably whole blood, plasma, serum, amniotic fluid, cerebrospinal fluid, ascites or urine, is obtained from a patient. The sample is then placed in contact with a system of detection capable of measuring the presence of the cleaved peptide fragment of a thrombin receptor. The presence or absence of the cleaved peptide fragment of a thrombin receptor is detected and the amount of cleaved peptide fragment is quantitated so that a pre-thrombotic state in the patient can be diagnosed.

Many different systems of detection can be used to measure the cleaved peptide fragment. Both competitive and non-competitive binding assays can be employed. For example, techniques such as radioimmunoassays (RIA), enzyme immunoassays (EIA), enzyme linked immunosorbent assays (ELISA), "sandwich" immunoassays, precipitin reactions, gel diffusion reactions, immunodiffusion assays, agglutination assays, complement-fixation assays, immunoradiometric assays, fluorescent immunoassays, fluorescence polarization, protein A immunoassays, and immunoelectrophoresis assays, can all serve as systems of detection in the present invention.

In one embodiment, the system of detection capable of measuring the presence of the cleaved peptide fragment in a sample is based upon standard ELISA technology. There are a variety of methods to do an ELISA, all of which are well-known to those of skill in the art. One method is referred to as an "antigen capture" method in which a solid phase support coated, with an antibody against the cleaved peptide fragment is contacted with a sample containing an unknown amount of the cleaved peptide fragment. The term "solid phase support" refers to any support capable of binding an antigen or antibodies. A preferred solid phase support used in ELISA assays is a plastic microtiter plate. Binding of the peptide to the antibody-coated support is then detected with a second antibody directed against a different portion of the cleaved peptide fragment than the first antibody. The precise amount of cleaved peptide fragment present in a sample is then determined from a standard curve. Assays based upon this type of technology are in widespread use in clinical laboratories. A variety of techniques can be used to detect the binding of the second antibody.

In another embodiment, wherein the system of detection is based upon a "sandwich" immunoassay, a monoclonal antibody to the cleaved peptide fragment is bound to a solid phase. A sample is then contacted with the solid phase and any cleaved peptide fragment in the sample is captured by the bound monoclonal antibody. A polyclonal antibody which will bind to the cleaved peptide fragment can then be placed in contact with the plate. The amount of cleaved peptide fragment in the sample can then be determined by detecting the amount of the bound polyclonal antibody. Various means for detecting the polyclonal antibody are well known in the art.

In another embodiment, wherein the system of detection is based upon (EIA) techniques, an enzyme is used to detectably label an antibody capable of binding the cleaved peptide fragment. Examples of enzymes include, but are not limited to, horse radish peroxidase, alkaline phosphatase, glucose-6-phosphate dehydrogenase, malate dehydrogenase, staphylococcal nuclease, yeast alcohol dehydrogenase, triose phosphate isomerase, asparaginase, glucose oxidase, β-galactosidase, ribonuclease, urease, catalase, glucoamylase and acetylcholinesterase.

In another embodiment, an antibody against the cleaved peptide fragment is labeled with a fluorescent compound, the presence of which can be detected by exposure to light at the proper wavelength. Examples of commonly used fluorescent labels include, but are not limited to, fluorescein isothiocyanate, rhodamine, phycoerythrin, phycocyanin, allophycocyanin, o-phthaldehyde and fluorescamine.

In yet another embodiment, the antibody is coupled to a chemiluminescent compound, the presence of which is determined by detecting the presence of luminescence that arises during the course of a chemical reaction. Examples of chemiluminescent compounds commonly used as labels include, but are not limited to, luminol, isoluminol, theromatic acridinium ester, imidazole, acridinium salt and oxalate ester. A bioluminescent protein can also be used to label the antibody. Examples of bioluminescent labels include, but are not limited to, luciferin, luciferase and aequorin.

Radionuclides can also be used to detectably label the antibody.

Figure 3:
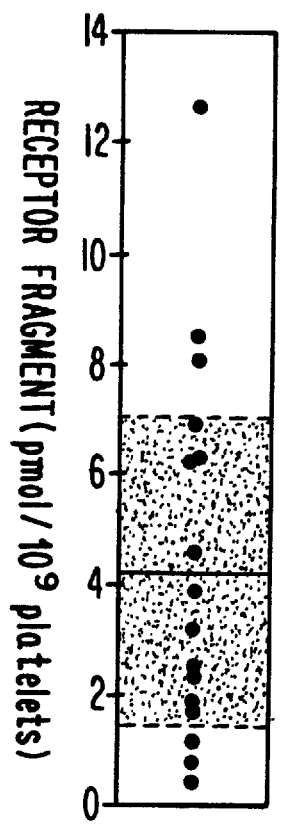
FIG. 3 shows concentrations of receptor fragment released from thrombin-treated platelets from 15 donors determined using a system of detection based upon competition between an unknown amount of the receptor fragment and a fixed amount of Peptide 1 (SEQ ID NO: 2) bound to a microtiter plate for binding to a limited amount of antibody PC143.

In a preferred embodiment, the presence of the cleaved peptide fragment is determined using a system of detection based upon competition between an unknown amount of the cleaved peptide fragment and a fixed amount of Peptide 1 (SEQ ID NO: 2) bound to a microtiter plate for binding to a limited amount of a monoclonal antibody to the cleaved peptide fragment. For example, experiments were performed wherein the cleavage fragment was detected by its ability to compete with immobilized Peptide 1 (SEQ ID NO: 2) for a limited amount of antibody PC143. With this antibody and standards comprising free peptide 1, the assay was linear from 10 to 500 nM. FIG. 3 shows the accumulated results that were obtained when washed human platelets were incubated with thrombin and the cell supernates were assayed for the presence of the receptor fragment. The results are expressed as pmol of receptor fragment per $10^9$ platelets. For the 15 normal donors that were studied, the mean amount of receptor fragment detected was 4.4 pmol/$10^9$ platelets, which agrees very closely with the amount of fragment estimated from the known number of thrombin receptors per platelet (4.2×109 pmol/platelet).

Development of systems of detection are dependent upon the availability antibodies capable of specifically binding the cleaved peptide fragment. The term "specifically binding" refers to the binding which occurs between an antibody and its recognized antigen to which the antibody was produced. This type of binding is contrasted to non-specific binding wherein the antibody associates with anything other than the antigen to which it was prepared. Examples of non-specific-binding include: (1) sticking of the antibody to other proteins via sites other than the antigen combining site; (2) Fc-mediated interactions; and (3) interactions with molecules other than the thrombin receptor which contain linear amino acids sequences similar to that used for the antibody preparation. Experimentally, non-specific binding occurs in the absence of the defined antigen or still occurs after preincubation of the antibody with an excess of the immunizing peptide.

Antibodies capable of specifically binding the cleaved peptide fragment are prepared using standard hybridoma technology. Mice are immunized with peptides corresponding to the cleaved receptor fragment that have been coupled to a carrier such as KLH or autologous serum albumin. Once it has been determined that the mice are producing antibodies against the fragment, the mice are splenectomized and fused to cell lines used to prepare hybridomas. Antibodies in the hybridoma culture supernatants are screened for anti-peptide activity by ELISA and then mapped for their precise epitope. These antibodies can also be used in immunohistochemistry in techniques well known by those of skill in the art.

The methods of the present invention can also be used to assess the ability of an agent to modulate thrombin-induced cell activation. Thrombin-induced cell activation, determined by methods of the present invention, can be measured prior to and following administration of (1) anti-coagulants such as coumadin, (2) antithrombin agents such as heparin or hirudin derivatives, or (3) inhibitors of thrombin receptor activation that work by blocking the cleavage of the receptor by thrombin. The ability of such agents to modulate thrombin-induced cell activation can then be determined by comparing levels of activation before and after treatment.

Kits comprising one or more containers or vials comprising components for carrying out the systems of detection included in the present invention are also within the scope of this invention. Reagents necessary for carrying out the methods of the present invention are supplied as a kit which may include, for example, the necessary antibodies, standards and a solid phase support. In one embodiment a kit is provided comprising a solid phase support, preferably a plastic microtiter plate, a first antibody to the cleaved peptide fragment of the thrombin receptor, and a second antibody to the cleaved peptide fragment of the thrombin receptor wherein the second antibody is detectably labeled. Examples of detectable labels include, but are not limited to, enzymes, fluorescent compounds, chemiluminescent compounds, bioluminescent compounds, or radionuclides. In a preferred embodiment, the first antibody may be pre-absorbed to the solid phase support.

The following non-limiting examples are provided for illustrative purposes only.

EXAMPLES

Example 1

Production of Antibodies

Monoclonal Antibodies: Mice were immunized with Peptide 1 (SEQ ID NO: 2) (See FIG. 1) conjugated to KLH using glutaraldehyde. This immunization was followed by two subsequent booster injections. The mice were then bled and their serum was tested by ELISA for anti-peptide activity. Mice testing positive were given another booster injection. The spleens were then removed and hybridomas were formed by standard methods. The hybridoma supernatants were screened by ELISA against Peptide 1. Those testing positive were then screened for their ability to bind to thrombin receptors expressed on the surface of untreated megakaryoblastic cells such as HEL cells (ATCC catalog #TIB180) or CHRF-288 cells but not bind to the same cells following incubation with thrombin or to lymphoid cells that do not normally express thrombin receptors. As a final step in localizing the epitopes of the antibodies the ELISA was repeated using Peptide 2 (SEQ ID NO: 3) (See FIG. 1), as well as Peptide 1. Antibody PC143 was found to bind only to Peptide 1 while antibodies PC42 and PC108 bind to both Peptide 1 and Peptide 2, indicating the approximate locations of their epitopes that are shown in FIG. 1.

Polyclonal Antibodies: Using methods well-known in the art, rabbits are also immunized with Peptide 1 (SEQ ID NO: 2) (See FIG. 1) conjugated to KLH using glutaraldehyde or a synthetic peptide comprising the C-terminal half of Peptide 2 (ATLDPR; SEQ ID NO: 4) and a cysteine group used to conjugate the R-residue of SEQ ID NO: 4 to a carrier. Immunization with one of these peptides is followed by subsequent booster injections. The rabbits are then bled and their serum tested for anti-peptide activity.

Example 2

Platelet Preparation

Blood (100–200 ml) was obtained by clean venepuncture from healthy volunteers and drawn directly into a syringe containing acid-citrate-dextrose (20 ml/100 ml of blood). Platelet rich plasma was prepared by centrifugation for 15 minutes at 169 g. Erythrocytes and leukocytes were discarded, after which $PGE_1$ (1 μM) and aprotinin (2.2 μg/ml) were added. The platelets were then isolated by centrifugation at 1200 g for 20 minutes and re-suspended in 50 ml of HEPES-Tyrode's buffer (129 mM NaCl, 2.8 mM KCl, 8.9 mM $NaHCO_3$, 5.6 mM glucose, 0.8 mM $MgCl_2$, 0.8 mM $KH_2PO_4$, 10 mM HEPES, pH 7.35) containing 1 μM $PGE_1$, 1 mM EGTA, and 2.2 μg/ml aprotinin. This process was repeated, after which the plates were resuspended ($3–10\times10^9$ platelets/ml) in 1–2 ml of HEPES-Tyrode's buffer supplemented with $PGE_1$ (1 μM), EGTA (1 mM) and aprotinin (2.2 μg/ml).

Example 3

Immunofluorescence Microscopy

HEL or CHRF-288 cells were incubated at 37° C. in the presence or absence of either 5 units/ml thrombin or 50 μM SFLLRN. The cells were then cytocentrifuged onto glass sides, fixed with methanol:acetone (50:50), and stained with primary antibody. Antibody binding was detected with FITC-conjugated goat anti-mouse IgG (Tago, Burlingame, Calif.)

Example 4

Flow Cytometry

HEL or CHRF-288 cells were incubated at 37° C. in the presence or absence of thrombin (up to 5 units/ml). The cells ($2\times10^6$ cells/ml in RPMI 1640 without fetal calf serum) were then fixed in 1% paraformaldehyde, kept on ice for 30 minutes and then washed and resuspended in staining buffer (PBS, 0.02% sodium azide, 0.2% BSA, pH 7.4). Primary antibodies were added in the form of either undiluted hybridoma culture supernate, an optimal dilution of ascites (1:400 to 1:1000) or as a purified protein (10 μg/ml). After a 30 minute incubation with the primary antibody, the cells were washed again, incubated with a 1:40 dilution of FITC-labeled goat anti-mouse IgG for an additional 30 minutes and then fixed in 4% paraformaldehyde for subsequent analysis.

Platelets were prepared as described in Example 2. One hundred microliters of platelets were incubated for 10 minutes at room temperature with or without thrombin. Antibody (1 μg/ml of purified protein or 20 μl of undiluted hybridoma culture supernatant) was then added and the platelet suspension was placed at 4° C. for 15 minutes. Five hundred microliters of THEE was added and the platelets were sedimented at 1200 g for 5 minutes, This step was repeated. The platelets were then resuspended in 100 μl THEE to which 3 μl of FITC-labeled goat anti-mouse IgG (1:40 dilution) (Bio Source International, Camarillo, Calif.) was added. After a 15 minute incubation with the secondary antibody at 4° C., the platelets were diluted with 500 μl THEE, sedimented at 1200 g for 5 minutes, resuspended in 500 μl THEE and analyzed on a FACScan flow cytometer (Becton Dickinson, Mountain View, Calif.).

Example 5

Detection of Thrombin Receptor Cleavage

HEL or CHRF-288 cells were incubated with thrombin for 10 minutes at either 37° C. or 4° C. and the binding of the anti-receptor antibodies was measured by flow cytometry. Incubation with thrombin at 37° C. causes receptor cleavage and internalization. Incubation at 37° C. resulted in complete loss of binding sites for all antibodies against the thrombin receptor. At 4° C. internalization of the receptor is retarded, however, cleavage remains relatively the same. In these incubations there was a greater loss in binding of antibodies specific to the cleaved peptide fragment (PC42) of the thrombin receptor compared to binding of antibodies specific to other areas of the receptor thus indicating that the cleaved peptide fragment is lost from the surface of the cell following cleavage.

Figure 2:
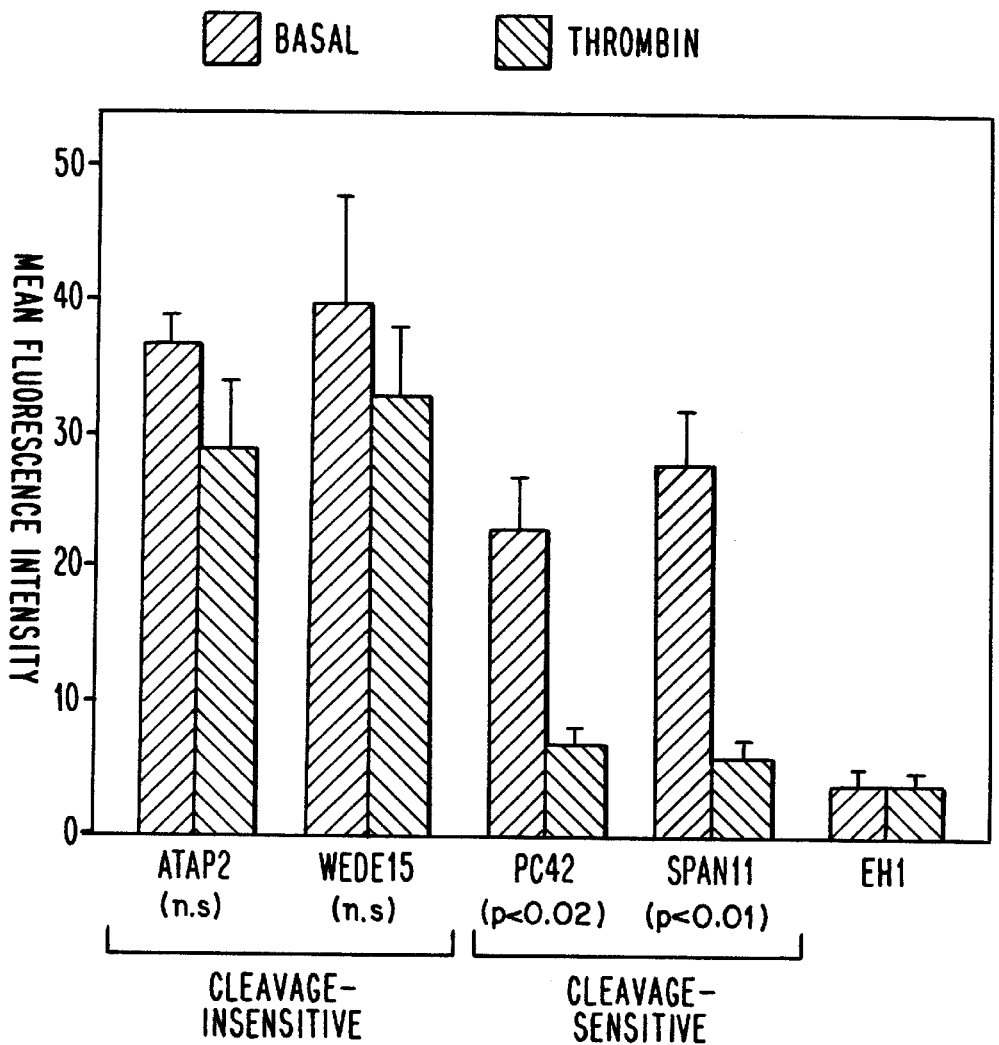
FIG. 2 shows the binding of antibody PC42, an antibody capable of specifically binding the cleaved peptide fragment, to platelets before and after incubation with thrombin. The other antibodies are peptide directed antibodies against other domains in the receptor N-terminus. ATAP2 and WEDE15 were prepared against peptides corresponding to residues 42–55 and 51–64, respectively. Their epitopes are present in resting as well as cleaved receptors. Antibody SPAN11 was raised against a peptide corresponding to residues 35–46, which span across the cleavage site. While SPAN 11 only binds to intact receptors, it does not recognize the cleaved peptide fragment. Antibody EH1 is an isotype-matched antibody raised against a viral protein and is used as a negative control.

Binding of antibodies was also examined in platelets before and after incubation with thrombin (see FIG. 2). The results in FIG. 2 indicate that on platelets, where activated thrombin receptors are not internalized, thrombin had no significant effect on the binding of the cleavage-insensitive antibodies (ATAP2, WEDE15 and EH1), but abolished the binding of PC42 and SPAN 11. Thus, incubation of platelets with thrombin significantly decreased binding of antibody PC42, the antibody capable of specifically binding the cleaved peptide fragment.

Example 6

Thrombin Receptor Fragment Assay

Washed platelets, prepared in accordance with Example 2, were incubated with or without thrombin (0.5 u/ml) for 10 minutes at room temperature, after which EDTA (1 mM), leupeptin (10 μg/ml) and PMSF (100 μg/ml) were added. The platelets were then sedimented by centrifugation at 8000 g for 5 minutes and the cell supernate removed for analysis of the thrombin receptor fragment. Microtiter plate wells were pre-coated by adding 50 μl of Peptide 1 (SEQ ID NO: 2), incubating for 2 hours at room temperature, and washing three times with PBST (PBS plus 0.05% Tween 20). The plates were then blocked by adding 200 μl of 2% BSA in PBS with 0.05% NaN3, incubating for 2 hours at room temperature and washing three times with PBST. Standards containing Peptide 1 (SEQ ID NO: 2) were prepared in PBS with 1% BSA, as were the antibody working stocks. The amount of receptor fragment that was present in the platelet supernate was then determined by competition between the fragment and the synthetic peptide coated on the microtiter plate for binding to a limited amount of antibody. Antibody PC143 (5–10 ng/ml final concentration) was added to either the peptide standard or platelet supernate, and then 50 μl of the combination was added to replicate wells of the peptide-coated microtiter plate. The plate was then incubated overnight at 4° C. or 2 hours at room temperature and washed three times with PBST. Antibody bound to the plate was detected using biotinylated goat anti-mouse antibody (Sigma Chemical Co., St Louis, Mo.) followed by an anti-biotin-alkaline phosphate conjugate (Sigma Chemical Co.) and the fluorescent substrate, ATTOPHOS (JBL Scientific Inc., San Luis Obispo, Calif.). The plates were read using CYTOFLOUR (PerSeptive Biosystems, Framingham, Mass.). The results of the unknown samples are in arbitrary fluorescence units which are converted to moles of peptide using the standard curve included in each assay.

What is claimed:

1. A method of diagnosing a pre-thrombotic state in a patient comprising:

(a) obtaining a sample comprising whole blood, serum, plasma or urine from a patient;

(b) contacting a solid phase support coated with a peptide consisting of SEQ ID NO: 2 with the sample and a known amount of an antibody which specifically binds to the peptide consisting of SEQ ID NO: 2 so that the peptide consisting of SEQ ID NO: 2 and any peptide fragment comprising the N-terminal fragment of the thrombin receptor cleaved by thrombin between residues $Ser^{42}$ and $Arg^{41}$ in the sample can specifically bind to the antibody;

(c) detecting any antibody bound specifically to the peptide consisting of SEQ ID NO: 2 on the solid phase support; and (d) quantifying the amount of peptide comprising the N-terminal fragment of the thrombin receptor cleaved by thrombin between residues $Ser^{42}$ and $Arg^{41}$ in the sample based on an amount of specifically bound antibody detected so that a pre-thrombotic state in the patient can be diagnosed.

2. A kit useful for detecting thrombin-induced cell activation and diagnosing a pre-thrombotic state in a patient comprising:

(a) a solid phase support;

(b) a peptide consisting of SEQ ID NO: 2; and (c) a monoclonal antibody which specifically binds to the peptide consisting of SEQ ID.NO: 2.

3. A method of detecting thrombin-induced cell activation in a subject comprising:

(a) obtaining a sample of whole blood, serum, plasma or urine from the subject;

(b) contacting a solid phase support which has been coated with a peptide consisting of SEQ ID NO: 2 with the sample and a known amount of an antibody which specifically binds to the peptide consisting of SEQ ID NO: 2; and (c) detecting any antibody specifically bound to the peptide consisting of SEQ ID NO: 2 on the solid phase support so that the presence or absence of a peptide comprising the N-terminal fragment of a thrombin receptor cleaved by thrombin between residues $Ser^{42}$ and $Arg^{41}$ which is indicative of thrombin-induced cell activation can be determined.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 46
        ( B ) TYPE: amino acid
        ( D ) TOPOLOGY: linear ( x i ) SEQUENCE DESCRIPTION: SEQ ID NO: 1:

```
Leu Leu Ser Ala Arg Thr Arg Ala Arg Arg Pro Glu Ser Lys Ala
1               5                   10                  15
Thr Asn Ala Thr Leu Asp Pro Arg Ser Phe Leu Leu Arg Asn Pro
                20              25                      30
Asn Asp Lys Tyr Glu Pro Phe Trp Glu Asp Glu Glu Lys Asn Glu
                35              40                      45
Ser
```

( 2 ) INFORMATION FOR SEQ ID NO: 2:

( i ) SEQUENCE CHARACTERISTICS:
        ( A ) LENGTH: 16
        ( B ) TYPE: amino acid
        ( D ) TOPOLOGY: linear ( x i ) SEQUENCE DESCRIPTION: SEQ ID NO: 2:

```
Leu Leu Ser Ala Arg Thr Arg Ala Arg Arg Pro Glu Ser Lys Ala
1               5                   10                  15
Thr
```

( 2 ) INFORMATION FOR SEQ ID NO: 3:

( i ) SEQUENCE CHARACTERISTICS:
        ( A ) LENGTH: 15
        ( B ) TYPE: amino acid
        ( D ) TOPOLOGY: linear ( x i ) SEQUENCE DESCRIPTION: SEQ ID NO: 3:

```
Arg Arg Pro Glu Ser Lys Ala Thr Asn Ala Thr Leu Asp Pro Arg
1               5                   10                  15
```

( 2 ) INFORMATION FOR SEQ ID NO: 4:

( i ) SEQUENCE CHARACTERISTICS:
        ( A ) LENGTH: 6
        ( B ) TYPE: amino acid
        ( D ) TOPOLOGY: linear ( x i ) SEQUENCE DESCRIPTION: SEQ ID NO: 4:

```
Ala Thr Leu Asp Pro Arg
1               5
```